(12) United States Patent
Fisher et al.

(10) Patent No.: US 8,267,853 B2
(45) Date of Patent: Sep. 18, 2012

(54) SYSTEM AND METHOD FOR OVERLAYING ULTRASOUND IMAGERY ON A LAPAROSCOPIC CAMERA DISPLAY

(75) Inventors: James Brian Fisher, San Antonio, TX (US); Steven P. Bowers, Ponte Vedra Beach, FL (US); Kent R. Van Sickle, San Antonio, TX (US); Warren Carl Couvillion, Jr., San Antonio, TX (US); Robert D. Wright, Conroe, TX (US); Jeremy W. Cannon, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 1093 days.

(21) Appl. No.: 12/144,443

(22) Filed: Jun. 23, 2008

(65) Prior Publication Data

US 2009/0318756 A1 Dec. 24, 2009

(51) Int. Cl.
*A61B 1/00* (2006.01)
*A61B 1/04* (2006.01)
(52) U.S. Cl. ........ 600/113; 600/103; 600/109; 600/117; 600/118; 348/45
(58) Field of Classification Search .................. 600/103, 600/109, 117–118, 424–425, 204; 348/45; 396/17
See application file for complete search history.

(56) References Cited

U.S. PATENT DOCUMENTS

| | | | |
|---|---|---|---|
| 6,019,724 A * | 2/2000 | Gronningsaeter et al. | 600/439 |
| 2001/0035871 A1 * | 11/2001 | Bieger et al. | 345/630 |
| 2004/0030367 A1 * | 2/2004 | Yamaki et al. | 607/60 |
| 2005/0027187 A1 * | 2/2005 | Barth et al. | 600/407 |
| 2005/0033117 A1 * | 2/2005 | Ozaki et al. | 600/109 |
| 2005/0085718 A1 * | 4/2005 | Shahidi | 600/424 |
| 2005/0168476 A1 * | 8/2005 | Levene et al. | 345/582 |
| 2008/0030578 A1 | 2/2008 | Razzaque et al. | |
| 2008/0058835 A1 * | 3/2008 | Farritor et al. | 606/130 |

OTHER PUBLICATIONS

Bao, et al., "Ultrasound-to-computer-tomography registration for image-guided laparoscopic liver surgery," Surg Endosc (2005) 19: 424-429.
Ellsmere, et al., "A Navigation System for Augmenting Laparoscopic Ultrasound," Medical Image Computing and Computer-Assisted Intervention—MICCAI 2003, vol. 2879/2003, 2003, 184-191.

(Continued)

*Primary Examiner* — John P Leubecker
*Assistant Examiner* — Arnaldo Torres Diaz
(74) *Attorney, Agent, or Firm* — Grossman Tucker et al

(57) ABSTRACT

The present disclosure relates to a system for overlaying ultrasound imagery on a laparoscopic camera display. The system may include a laparoscope configured to capture a laparoscopic image of a surgical field and a laparoscopic ultrasound probe configured to capture an ultrasonic image of a structure in the surgical field. The system may further include a tracking system configured to detect a position and orientation of the laparoscope and a position and orientation of the laparoscopic ultrasound probe. The system may further include data associated with the laparoscope wherein the data indicates a distortion in the laparoscopic image. The system may further include a computer configured to receive the laparoscopic image, the ultrasonic image and the distortion data associated with the laparoscope. The computer may be configured to position and orient the ultrasonic image relative to the laparoscopic image, adjust the ultrasonic image based upon the distortion data, combine the adjusted ultrasonic image with the laparoscopic image, and output the combined images.

19 Claims, 6 Drawing Sheets

OTHER PUBLICATIONS

State, et al, "Stereo Imagery from the UNC Augmented Reality System for Breast Biopsy Guidance," available at http://www.cs.unc.edu/~andrei/pubs/2003_MMVR_stereos.pdf, retrieved on Nov. 7, 2008.

State, et al., "Virtual and Augmented Reality Visualization and Guidance for Minimally Invasive Surgery," Department of Computer Science University of North Carolina at Chapel Hill Aug. 2007, available at http://www.cs.unc.edu/Research/ProjectSummaries/visualizationsurgery0308.pdf, retrieved on Nov. 7, 2008.

Baumhauer, "Navigation in Endoscopic Soft Tissue Surgery: Perspectives and Limitations," Journal of Endourology, vol. 22, No. 4, Apr. 2008.

Maintz, et al., "A Survey of Medical Image Registration," Medical Image Analysis (1998) vol. 2, No. 1, pp. 1-37 c.

Shuhaiber, "Augmented Reality in Surgery," (Reprinted) Arch Surg/vol. 139, Feb. 2004 www.archsurg.com 170.

* cited by examiner

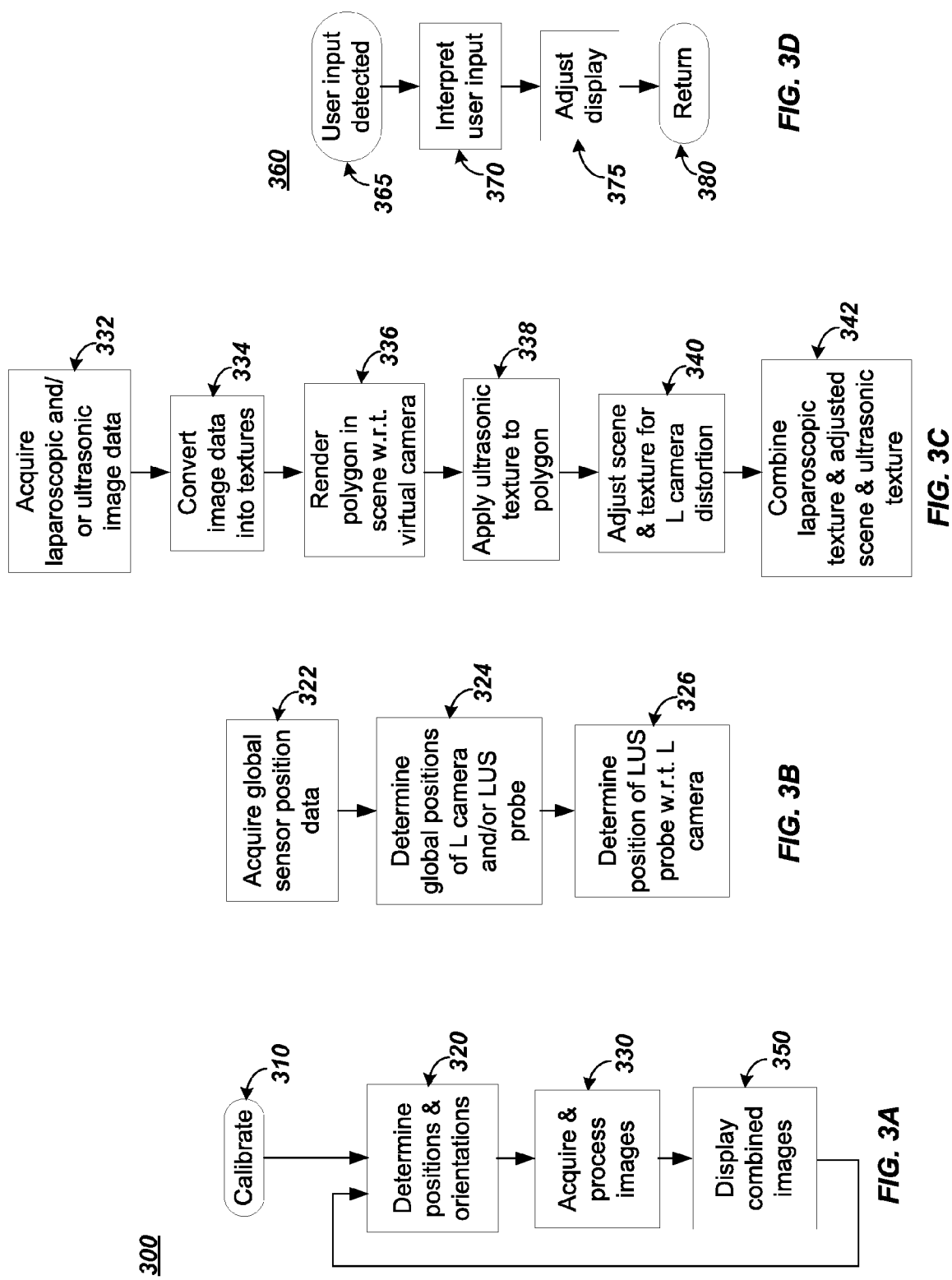

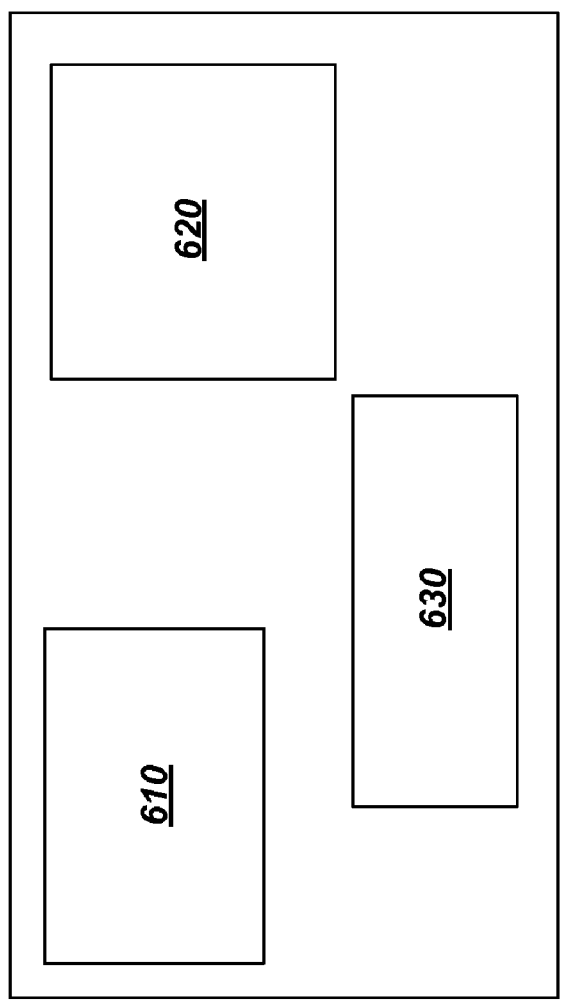

SYSTEM AND METHOD FOR OVERLAYING ULTRASOUND IMAGERY ON A LAPAROSCOPIC CAMERA DISPLAY

FIELD OF THE INVENTION

This disclosure relates to a system and method for overlaying ultrasound imagery on a laparoscopic camera display. The system and method may enable a user, e.g., a surgeon, to view correlated imagery from a tracked laparoscopic ultrasound device and laparoscope camera in real time in a combined display during minimally invasive surgical procedures.

BACKGROUND

During minimally invasive surgical procedures, instruments may be inserted into a patient through small incisions in the abdomen, for example. A relatively small video camera (e.g., laparoscope) may also be inserted into the abdomen. The laparoscope may then provide a magnified image of inside the body to a video monitor, for example. This magnified image may provide a user, e.g., a surgeon, a "close-up" view of organs, tissues and the like. The surgeon may then utilize this view to identify, and perform a surgical intervention on, an anatomical structure by manipulating the surgical instruments while watching the video display.

Accurately identifying key anatomical features may be challenging when relying solely on the laparoscopic camera view. For example, it is often difficult to distinguish certain anatomical features. Improper identification of anatomical features may result in serious complications. Laparoscopic ultrasound, an imaging technique, is a safe, quick and effective method for identifying anatomical structures during minimally invasive surgical procedures. For example, an ultrasound probe may be inserted through an additional incision in the abdomen and may then be manipulated to obtain ultrasound images showing desired anatomical structures.

It may be difficult for a surgeon to correlate the laparoscopic camera image and the laparoscopic ultrasound image as the images are typically displayed separately. It may be challenging for a surgeon to determine the position and orientation of an ultrasound image relative to the laparoscopic camera image. A method of correlating the two views may then be desirable.

SUMMARY

The present disclosure relates in one embodiment to a system for overlaying ultrasound imagery on a laparoscopic camera display. The system includes a laparoscope configured to capture a laparoscopic image of a surgical field and a laparoscopic ultrasound probe configured to capture an ultrasonic image of a structure in the surgical field. The system further includes a tracking system configured to detect a position and orientation of the laparoscope and a position and orientation of the laparoscopic ultrasound probe. The system further includes data associated with the laparoscope wherein the data indicates a distortion in the laparoscopic image. The system further includes a computer configured to receive the laparoscopic image, the ultrasonic image and the distortion data associated with the laparoscope. The computer is configured to position and orient the ultrasonic image relative to the laparoscopic image, adjust the ultrasonic image based upon the distortion data, combine the adjusted ultrasonic image with the laparoscopic image, and output the combined images.

The present disclosure relates in another embodiment to a method for overlaying an ultrasonic image on a laparoscopic image. The method includes retrieving data associated with a laparoscope wherein the data indicates a distortion in the laparoscopic image. The method further includes capturing the laparoscopic image of a surgical field using the laparoscope and capturing the ultrasonic image of the surgical field using a laparoscopic ultrasound probe. The method further includes detecting a position and orientation of the laparoscope and a position and orientation of the ultrasound probe, and positioning and orienting the ultrasonic image relative to the laparoscopic image. The method further includes adjusting the ultrasonic image based upon the distortion data, combining the adjusted ultrasonic image with the laparoscopic image, and outputting the combined images.

In yet another embodiment, the present disclosure relates to an article comprising a storage medium having stored thereon instructions that when executed by a machine result in the following operations for overlaying an ultrasonic image on a laparoscopic image: retrieving data associated with a laparoscope wherein the data indicates a distortion in the laparoscopic image, receiving the laparoscopic image of a surgical field captured using the laparoscope, receiving the ultrasonic image of the surgical field captured using a laparoscopic ultrasound probe, receiving a position and orientation of the laparoscope and a position and orientation of the ultrasound probe, positioning and orienting the ultrasonic image relative to the laparoscopic image, adjusting the ultrasonic image based upon the distortion data, combining the adjusted ultrasonic image with the laparoscopic image, and outputting the combined images.

BRIEF DESCRIPTION OF THE DRAWINGS

The detailed description below may be better understood with reference to the accompanying figures which are provided for illustrative purposes and are not to be considered as limiting any aspect of the invention.

FIGS. 3A through 3D depict illustrative flow charts of calibration and position sensing; acquisition, processing and display of images; and user input processing.

FIG. 6 illustrates an example of a system and method for overlaying ultrasound imagery on a laparoscopic camera display in real time that contains a processor, machine readable media and a user interface.

DETAILED DESCRIPTION

In general, the present disclosure describes a system and method for overlaying a laparoscopic ultrasound (LUS) image onto a laparoscopic camera image, which may be accomplished in real time. Reference to real time may be understood as performing the overlay onto said laparoscopic camera image while said camera is capturing an image. It may also be appreciated that ultrasound imagery may provide a subsurface view of an organ and/or tissue being imaged while a laparoscopic camera display may provide a surface view of the organ and/or tissue being imaged. The overlaid ultrasonic image may be positioned and oriented in the laparoscopic image relative to a LUS probe and/or a laparoscope. The overlaid ultrasonic image may be adjusted based on distortion that may be present in the laparoscopic camera image. The system and method may also provide a user interface, e.g., a graphical user interface (GUI), that allows a user to interactively view and/or manipulate the combined images.

Figure 1:
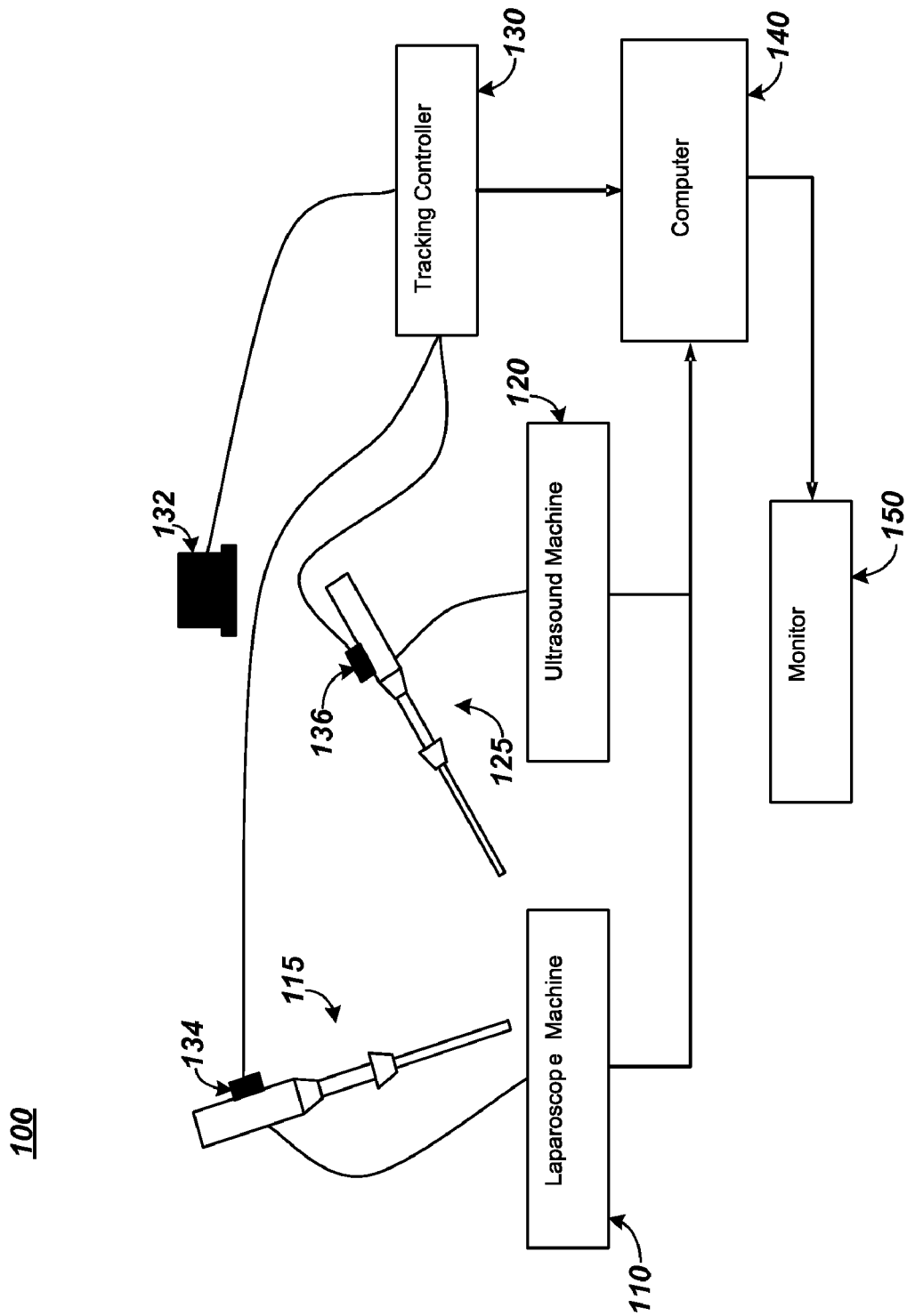
FIG. 1 depicts an illustrative system block diagram consistent with the present disclosure.

Attention is directed to FIG. 1 which depicts an illustrative system block diagram 100 of a system for overlaying ultrasonic imagery on a laparoscopic camera display in real time. The system 100 may include a laparoscope machine 110, an ultrasound machine 120, a tracking controller 130, a computer 140, e.g., a personal computer with video capture capability, and a monitor 150, i.e., display device. The monitor 150 may be integral with the computer 140 and/or may be separate. The tracking controller 130 may be coupled to a tracking transceiver 132 and one or more tracking sensors. A first tracking sensor 134 may be disposed in or on a laparoscope 115. The laparoscope 115 includes a camera (not explicitly shown). A second tracking sensor 136 may be disposed in or on a LUS probe 125. The system 100 is not limited to two cameras and/or probes nor is it limited to two tracking sensors. A number of tracking sensors may at least equal a number of probes and/or cameras that are desired to be tracked.

Figure 2B:
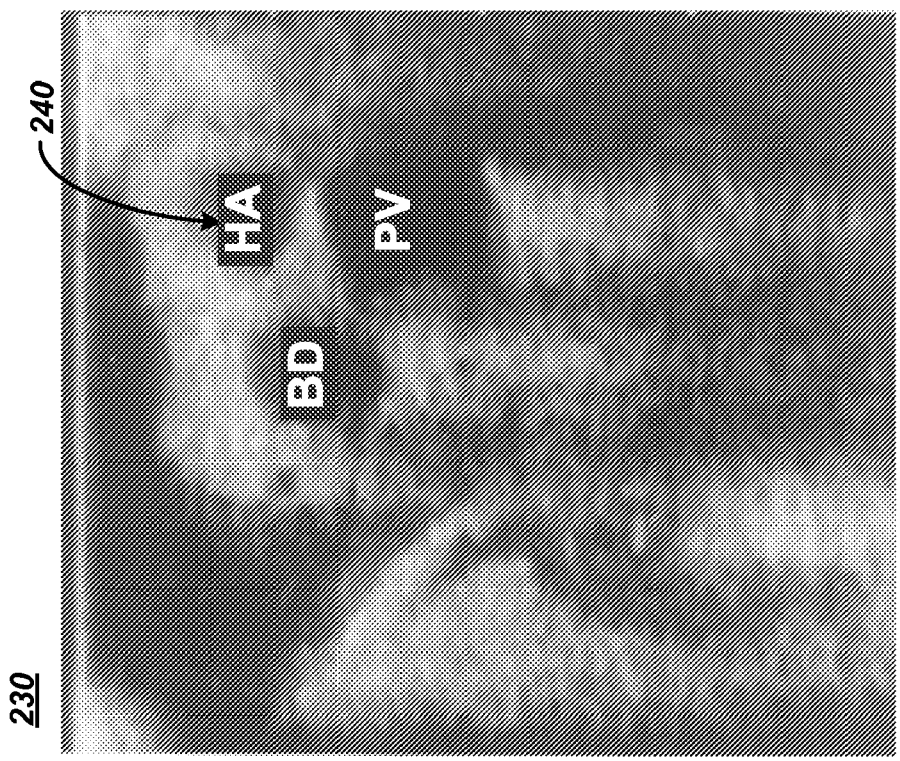
FIGS. 2A and 2B depict an illustrative sketch of a body portion with a laparoscope and a laparoscopic ultrasound probe and an illustrative ultrasound image with exemplary labels, respectively.
Figure 2A:
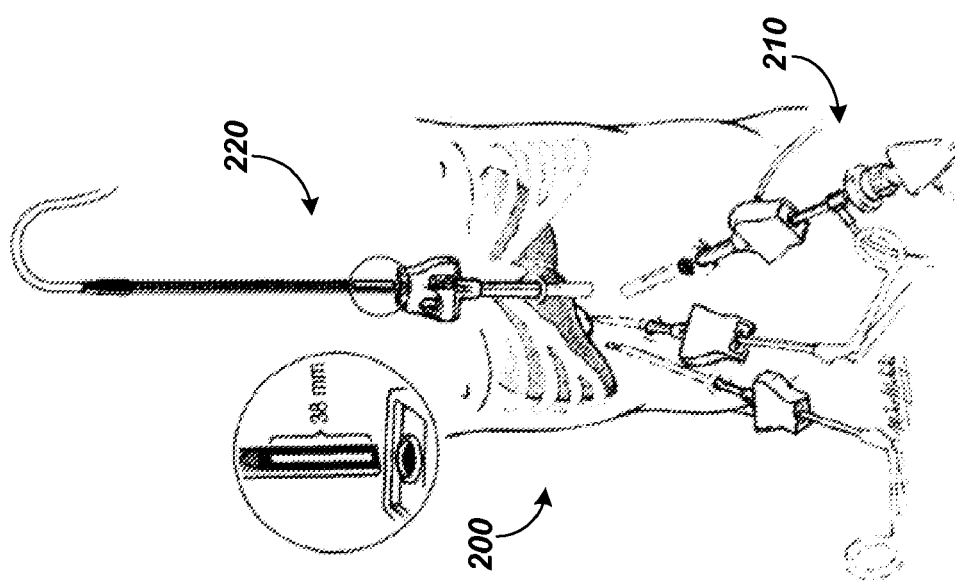

As depicted in FIG. 2A, for example, during a surgical procedure, e.g., a laparoscopic cholecystectomy (i.e., surgical removal of a gallbladder), a portion of a laparoscope 210 and a portion of a LUS probe 220 may be inserted into an abdomen 200. The laparoscope 210 may provide a user a camera view of a surgical field. The surgical field may include structures including organs, tissue, blood vessels, and/or the like. The laparoscope 210 may provide a surface view of the organs, etc., that are present in the laparoscope's field of view. At least a portion of the LUS probe 220 may be positioned in the surgical field. The LUS probe 220 may provide a subsurface view of a selected structure, e.g., an organ and/or tissue. The LUS probe 220 may provide a two-dimensional "slice" and/or a three-dimensional volume view of the organ and/or tissue. FIG. 2B. depicts an illustrative two-dimensional ultrasonic image 230. The image 230 has been annotated 240 to indicate certain structures, e.g., HA (hepatic artery), BD (bile duct) and PV (portal vein).

Continuing now with reference to FIG. 1, the laparoscope 115 may capture an image of the surgical field. This image may be provided to the laparoscope machine 110 and then to the computer 140. The LUS probe 125 may capture an ultrasonic image of a structure in the surgical field. This ultrasonic image may be provided to the ultrasound machine 120 and then to the computer 140. Accordingly, a laparoscope herein may be understood as any device configured to image an internal body region and/or internal structure (i.e., internal body part). A laparoscope ultrasonic probe may be similarly understood as any device that is configured to provide an ultrasonic image of an internal body region and/or internal structure (i.e., internal body part). Reference to surgical field herein may therefore be understood as an internal body region including a structure, i.e. an internal body part.

It may be appreciated that the laparoscope 115 provides a two-dimensional image of a three-dimensional view. The two-dimensional image may depend on the position of the laparoscope camera as well as camera properties, e.g., distortion. Laparoscope cameras may be subject to lens distortion. In particular, laparoscopes may have "fish-eye" lenses, that may introduce "barrel" distortion in a laparoscopic image. In barrel distortion, a straight line may appear curved with the degree of curvature increasing with distance from the center of the view. Degree of curvature may therefore be understood as a length of a radius for the curve that is identified. The curve may be concave relative to the center of the image. In other words, a straight line in the surgical field viewed through a fish-eye type lens may appear curved in the laparoscopic image of the surgical field. Accordingly, distortion herein may be understood as a difference (e.g. a straight line appearing as a curved line as noted above) as between the actual image of a given internal body region and/or structure and the captured image provided by the laparoscope.

The first tracking sensor 134 may provide a position (e.g., x, y, and z) and an orientation (e.g., pitch, roll and yaw) of the laparoscope 115 relative to the tracking transceiver 132. This first sensor 134 position and orientation data may be provided to the tracking controller 130. The second tracking sensor 136 may provide a position and an orientation of the LUS probe 125 relative to the tracking transceiver 132. This second sensor 136 position and orientation data may be provided to the tracking controller 130. The tracking controller 130 may then provide tracking information to the computer 140.

The tracking system, i.e., tracking controller 130, tracking transceiver 132 and tracking sensors 134 and 136, may include electromagnetic, optical and/or mechanical tracking. In an electromagnetic tracking system, the tracking transceiver 132 may include one or more electromagnetic generators configured to generate orthogonal electromagnetic fields. In this configuration, each tracking sensor 134, 136 may be capable of detecting position and orientation based on the orthogonal electromagnetic fields. In an optical tracking system, the tracking transceiver 132 may include one or more cameras configured to detect light. In one embodiment, the tracking transceiver 132 may emit a beam of light that may be reflected by each tracking sensor 134, 136. In this embodiment, each tracking sensor 134, 136 may include a passive retroreflector that reflects incident light parallel to a direction of the incident light. In another embodiment, each tracking sensor 134, 136, may include an active light emitting device, e.g., a light emitting diode. Light from the light emitting device may be detected by the tracking receiver 132. In a mechanical tracking system, position and orientation may be detected using a direct mechanical connection to the laparoscope 115 and LUS probe 125. In this embodiment, the laparoscope 115 and LUS probe 125 may be mounted to mechanical members coupled by joints with six degrees of freedom (e.g., x, y and z, and pitch, roll and yaw). The tracking sensors 134, 136 may include encoders at each joint for detecting position and orientation of the laparoscope 115 and the LUS probe 125.

It may be appreciated that it is desirable to minimize the number of foreign bodies and/or amount of foreign matter that is introduced into a patient during a surgical procedure. As shown in FIG. 1, for example, the first and second tracking sensors 134, 136 may be disposed on the laparoscope 115 and the LUS probe 125, respectively, so that the sensors 134, 136 remain outside of the patient. As a result, the position and orientation of each tracking sensor 134, 136 may be physically offset from the image acquisition portion of its respective device, i.e., laparoscope camera lens and LUS probe tip where ultrasonic transducers may be located, respectively. The system 100 may be calibrated to account for these offsets to provide position and orientation of the laparoscope camera lens and the LUS probe tip.

Attention is directed to FIGS. 3A through 3D which depict illustrative flow charts consistent with the present disclosure.

FIG. 3A depicts an illustrative flow chart 300 for acquiring, processing and displaying combined laparoscopic and ultrasonic images. FIG. 3B depicts an embodiment of acquiring and/or determining laparoscope and LUS probe positions and/or orientations. FIG. 3C depicts an embodiment of acquiring, processing and combining laparoscopic and ultrasonic images for display. FIG. 3D depicts an exemplary flow chart 360 for detecting and responding to user inputs. It may be appreciated that although the flow charts indicate sequential steps, some steps may be performed in parallel and some steps may be performed in an order different from the order shown.

Prior to an acquisition, the system 100 may be calibrated. Calibrate 310 may include determining sensor position and/or orientation offsets and laparoscope camera properties, e.g., lens distortion. Using a graphic user interface (GUI) for example, a user may also enter and/or adjust sizes of displayed laparoscopic and/or ultrasonic images. The user may also enter laparoscope camera-specific information, e.g., field of view and/or aspect ratio.

In an embodiment, the system may be calibrated for lens distortion prior to a surgical setup. The laparoscope 115 may be held in a fixed position relative to a surface with a uniform grid, e.g., a piece of graph paper. An image of the uniform grid detected by the laparoscope camera may include distortion, i.e., the imaged grid may not appear uniform. The imaged grid may be rendered to a scene displayed to the user on a monitor, for example. A corresponding uniform grid (i.e., not distorted) may be rendered also to the scene and displayed to the user. The corresponding uniform grid may be rendered relative to a virtual camera positioned at a similar distance from the scene as the actual laparoscope camera is from the actual uniform grid. Using the GUI, the user may then adjust a distortion factor of the virtual camera until the corresponding grid lines of the imaged grid and the rendered uniform grid generally overlay one another. It may be appreciated that lens distortion is a property of the laparoscope camera and not the surgical setup. Data corresponding to lens distortion may be stored for later use.

The tracking sensors 134 and 136 may be calibrated initially, prior to and/or during a surgical procedure. An orientation of the first tracking sensor 134 relative to the laparoscope camera lens may be determined. A position of the first tracking sensor 134 relative to the laparoscope camera lens may then be determined. The process may be repeated for the second tracking sensor 136 relative to the LUS probe tip. Relative position and orientation data may be provided to the computer using the GUI and may provide position and orientation offsets for the laparoscope 115 and its respective tracking sensor 134 and for the LUS probe 125 and its respective tracking sensor 136.

The positions and orientations of the tracking sensors 134 and 136 may then be determined 320. A global position and/or orientation of each tracking sensor 134, 136 may be determined. A relative position and/or orientation of the laparoscope 115 and the LUS probe 125 may then be determined.

In an embodiment, determining the positions and orientations of the tracking sensors 320 may include acquiring global sensor position data 322. The positions and orientations of the tracking sensors 134 and 136 relative to the tracking transceiver 132 may be detected and provided to the computer 140. The global positions of the laparoscope 115 and LUS probe 125 may then be determined 324. As used herein, position and/or orientation of the laparoscope 115 may be understood to mean position and/or orientation of the image sensing portion of the laparoscope 115. Similarly, position and/or orientation of the LUS probe 125 may be understood to mean position and/or orientation of the LUS probe 125 ultrasonic transducers. The global positions and orientations of the laparoscope 115 and LUS probe 125 may depend on the sensed positions and orientations of the tracking sensors 134 and 136 and the calibration data. The position and orientation of the LUS probe 125 relative to the laparoscope 115 may then be determined 326.

Laparoscopic and/or ultrasonic image data may then be acquired and processed 330. Acquisition may include capturing images from the laparoscope 115 and/or the LUS probe 125. The captured ultrasonic image may then be processed according to the relative position and/or orientation of the laparoscope 115 and the LUS probe 125. This processing may orient and position the ultrasonic image relative to the laparoscopic image. In an embodiment, the image processing may include adjusting the ultrasonic image for distortion that may be present in the laparoscopic image (e.g., as a result of laparoscope camera lens distortion). The laparoscopic image and the adjusted ultrasonic image may then be combined based upon the relative position and orientation data.

In an embodiment, acquisition of laparoscopic and/or ultrasonic image data 332 may be via laparoscope machine 110 for the laparoscopic image and via the ultrasound machine 120 for the ultrasonic image. Each image may then be converted into a texture 334 for processing using a graphics processing unit (GPU), for example. A texture may correspond to an array of image data that is configured for storage and/or manipulation by a GPU. The GPU may be included in the computer 140.

A polygon may then be rendered 336 in a two-dimensional scene. The two-dimensional scene may correspond to a field of view of the laparoscope 115. In other words, the two-dimensional scene may be sized to correspond to the texture associated with the laparoscopic image. The polygon may be positioned and oriented relative to a virtual camera. The position and orientation relationship between the polygon and the virtual camera may correspond to the position and orientation relationship between the LUS probe 125 and the laparoscope 115. In an embodiment, the polygon may be rendered against a solid color, e.g., blue, background. A dimension (i.e., size) of the background may correspond to the field of view of the laparoscope camera. The texture corresponding to the ultrasonic image may then be applied to the polygon 338. The scene including the polygon containing texture corresponding to the ultrasonic image may then be adjusted (i.e., distorted) based on the distortion in the laparoscopic image 340. In this manner, the displayed ultrasonic image may be relatively more accurately registered to the displayed laparoscopic image by including laparoscopic camera lens-dependent distortion.

Figure 4B:
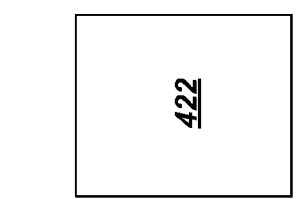
FIGS. 4A through 4D depict illustrative sketches of orienting and adjusting a laparoscopic ultrasound image for overlaying on a laparoscope display.
Figure 4D:
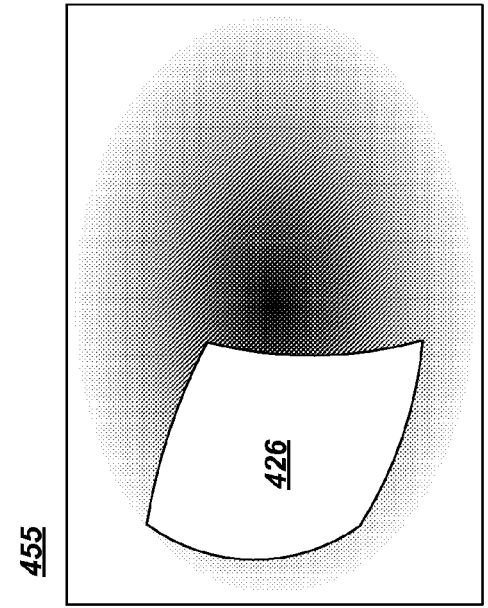
Figure 4A:
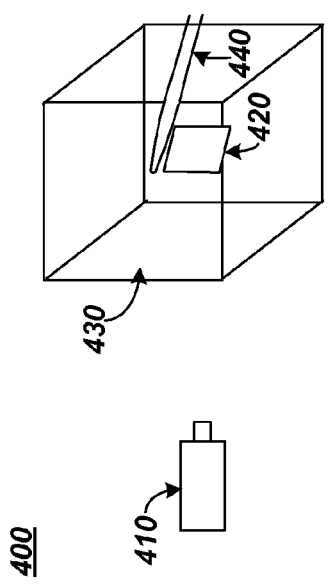
Figure 4C:
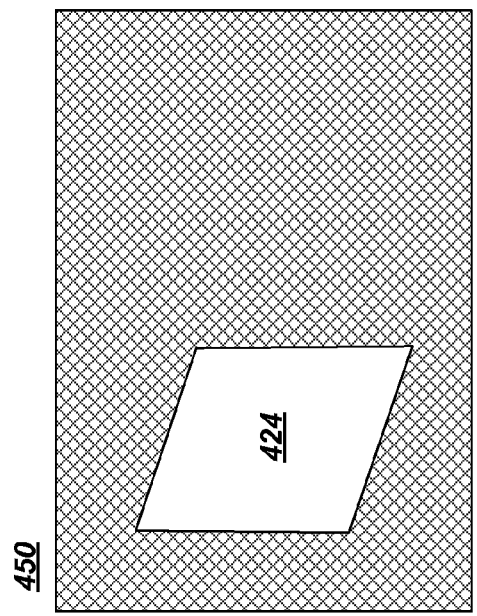

Attention is directed to FIGS. 4A through 4D which depict an illustrative example of positioning, orienting and distorting the texture corresponding to the ultrasonic image. FIG. 4A depicts a three-dimensional view 400 including a virtual camera 410 positioned relative to a three-dimensional scene 430 representing the laparoscope's 115 field of view. The three-dimensional scene 430 further includes a polygon 420 and a portion of an LUS probe 440. In this view, the polygon 420 is positioned and oriented relative to the LUS probe 440 and may indicate the position and orientation of an ultrasound image acquired by the LUS probe 440. FIG. 4B depicts a shape of an image 422 that may be acquired by a two-dimensional LUS probe, e.g., LUS probe 440. The image 422 may be rectangular. It may be appreciated that the shape of the image 422 may depend on the LUS technology used.

A polygon 424 corresponding to the image 422 may be rendered in a scene 450 relative to a virtual camera, e.g., virtual camera 410. It may be appreciated that the scene 450 may be two-dimensional to correspond to a display. Rendering a rectangle corresponding to the shape of the image 422, in the scene 450, may yield a polygon, e.g., polygon 424, depending on the position and orientation of the LUS probe 125 relative to the laparoscope 115. The scene 450 may correspond to the field of view of the laparoscope 115. The polygon 424 rendered in the scene may occupy only a portion of the scene 450. The portion of the scene 450 not occupied by the polygon 424 may be textured with a single color, e.g., blue, represented by the hatch marks in FIG. 4C. A texture corresponding to the ultrasonic image may then be applied to polygon 424.

The scene 450, including the polygon 424 containing the texture corresponding to the ultrasonic image, may then be adjusted based on the distortion that may be present in the laparoscopic image due to the laparoscope camera lens. As discussed above, data corresponding to laparoscope camera lens distortion may be determined and stored prior to a surgery. This distortion data may then be used to adjust the scene 450, including polygon 424 containing the texture corresponding to the ultrasonic image. FIG. 4D illustrates an example of this adjustment. Adjusting polygon 424 may yield a curved polygon 426 containing an adjusted texture corresponding to the ultrasonic image. The scene 455 corresponds to scene 450. As shown in FIG. 4D, the scene 455 including polygon 426 may include barrel-type distortion.

The texture corresponding to the laparoscopic image and the adjusted, oriented and positioned texture corresponding to the ultrasonic image may then be combined 342. In an embodiment, the textures may be combined using a shader (i.e., a program that runs on a GPU). For example, a first texture may correspond to the image from the laparoscope. A second texture may correspond to the ultrasonic image, positioned and oriented relative to the virtual camera on a single color background and adjusted (distorted) according to the laparoscope lens, e.g., scene 455.

The resulting texture, i.e., the combination of the texture corresponding to the laparoscopic image and the texture corresponding to the ultrasonic image may be displayed 350. The resulting texture may be displayed on the monitor 150, for example. These combined images may allow a user to view an ultrasonic image overlaid on a laparoscopic image. The laparoscopic ultrasound image may be oriented and positioned relative to the LUS probe so that it appears at the tip of the LUS probe. In other words, in the combined display, the ultrasonic image may be positioned and oriented to accurately represent the position and orientation of the ultrasonic image relative to the LUS probe in the view of the laparoscope. The process may then be repeated for each subsequent image. The images may be acquired, processed and displayed at a rate of about 30 frames per second.

The appearance, e.g., opacity, of the texture corresponding to the ultrasonic image may be adjusted by a user. An opacity setting, e.g., a translucency factor, may affect the display of the texture corresponding to the ultrasonic image. For example, a relatively low opacity setting may cause the polygon containing the texture corresponding to the ultrasonic image to be nearly transparent so that the texture corresponding to the laparoscopic image may be easily visible. A relatively high opacity setting may cause the polygon containing the texture corresponding to the ultrasonic image to be opaque so that the texture corresponding to the laparoscopic image may not be visible.

In an embodiment, the resulting texture may be generated as follows. If a texel in the first texture is the single color, e.g., blue, then that texel may be replaced with the corresponding texel from the second texture. If the texel in the first texture is not blue, then the texel may be combined with the corresponding texel from the second texture according to:

$$C_o = tC_s + (1-t)C_l$$

where
t is the translucency factor [0, 1];
$C_o$ is a combined texel;
$C_s$ is the first (i.e., ultrasonic image) texel; and
$C_l$ is the second (i.e., laparoscopic) texel.

As the translucency factor approaches 1, the polygon textured with the ultrasonic image appears opaque so that the laparoscopic image is not visible. As the translucency factor approaches 0, the polygon textured with the ultrasonic image appears translucent so that the laparoscopic image is visible. As discussed above, the translucency factor may be adjusted by the user.

Figure 5A:
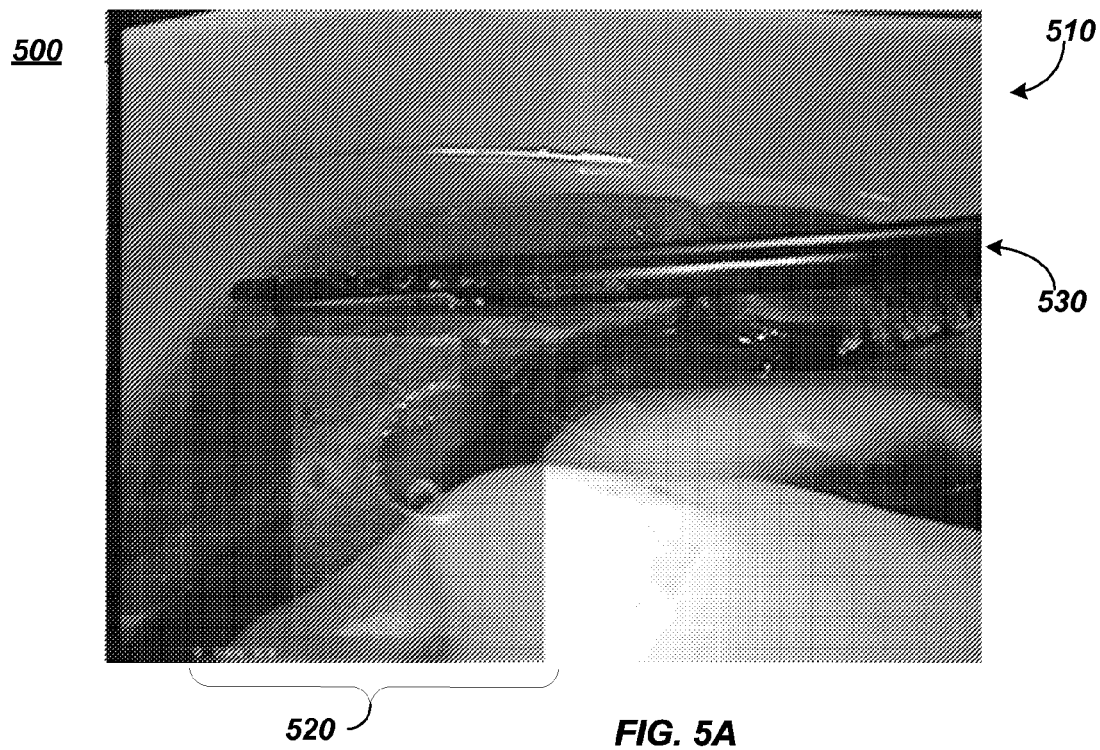
FIGS. 5A and 5B depict illustrative composite images with the laparoscopic ultrasound overlay at 50% and 95% opacity, respectively.
Figure 5B:
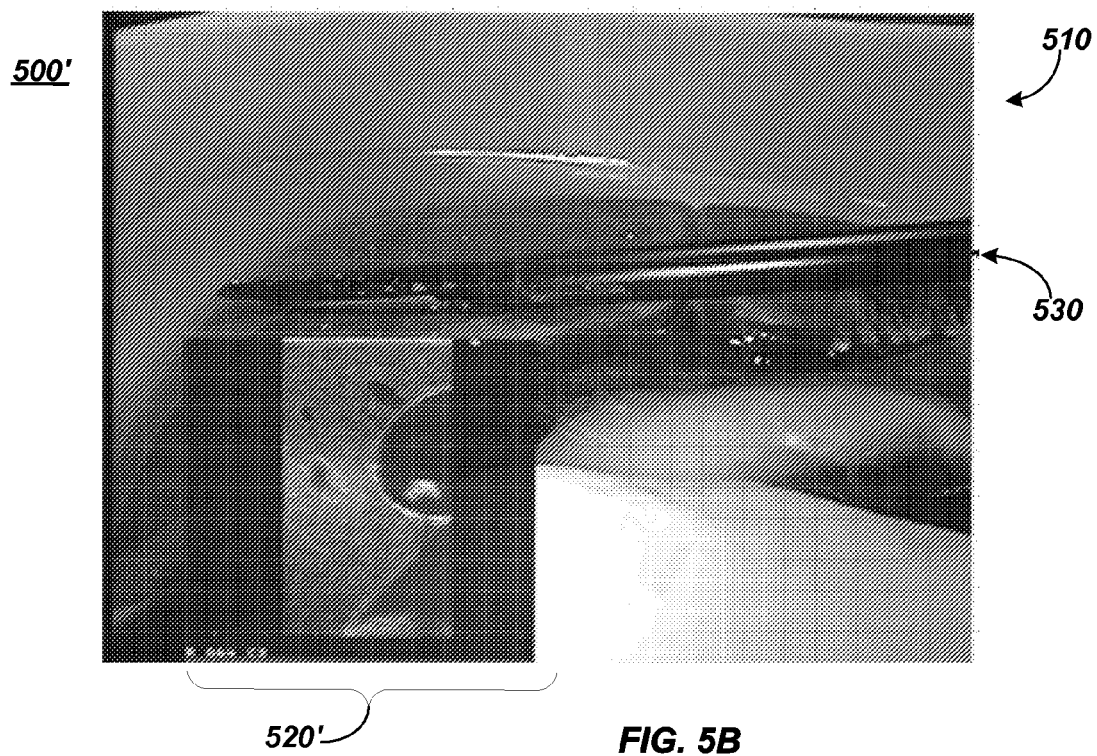

FIG. 5A depicts a combined image 500 with an opacity setting of about 50%. An ultrasonic image 520 is positioned and oriented relative to an LUS probe 530 in a laparoscopic image 510. At this opacity setting, a portion of the laparoscopic image 510 is visible "behind" the ultrasonic image 520. FIG. 5B depicts a combined image 500' with an opacity setting of about 95%. An ultrasonic image 520' is similarly positioned and oriented relative to the LUS probe 530 in the laparoscopic image 520. At this opacity setting, a portion of the laparoscopic image 510 is not visible behind the ultrasonic image 520'.

Attention is directed to FIG. 3D which depicts a simplified flow chart 360 for detecting and responding to user inputs. It may be appreciated that user inputs may occur at any time, e.g., when a user wishes to adjust a display. First, a user input may be detected 365. The detected user input may then be interpreted 370. Once the user input has been interpreted, the display may be adjusted accordingly 375. Program flow may then return 380.

It may be appreciated that the LUS probe 125 may be positioned and oriented so that the ultrasound image, when properly positioned and oriented relative to the LUS probe in the laparoscopic image, would appear as a line, i.e., as an edge of a polygon. In this situation, a user may wish to view the acquired ultrasonic image. In response to an appropriate user input, the acquired ultrasonic image may be displayed overlaid on the laparoscopic image near the position of the LUS probe tip. To provide the user with a visual cue that the displayed ultrasound image does not correspond to the actual orientation of the LUS probe, the image may be seen to "fly" to the probe tip. The user may toggle between the properly oriented ultrasonic image (i.e., edge, displayed as a line) and the acquired ultrasonic image (i.e., planar, displayed flying to probe tip).

It may be desirable to display more than one ultrasonic image on a laparoscopic image. It may be desirable to "freeze" one or more oriented and positioned ultrasonic images while continuing to acquire and display subsequent ultrasonic images. In an embodiment, when selected by a user, a current ultrasonic image may be "frozen" at its current orientation and position relative to the laparoscope. Once an ultrasonic image is frozen, it may remain in its frozen position, independent of further movement of the LUS probe. Multiple ultrasonic images may then be frozen on a laparoscopic image. The user may select this mode using the GUI and/or an appropriate control input device, e.g., switch, disposed on the LUS probe. The user may likewise exit this mode and/or clear (remove) the frozen ultrasonic images using the GUI and/or control input device on the LUS probe. In this manner, the user may be provided multiple LUS views of a structure, e.g., organ, tissue, blood vessel and/or the like, whose surfaces may be visible to the laparoscope.

In another embodiment, the user may annotate an ultrasonic image, e.g., as shown in FIG. 2B, prior to overlaying on the laparoscope view. In this way, features may be labeled to further aid a surgeon, for example, in accurately identifying key anatomical features.

It should also be appreciated that the functionality described herein for the embodiments of the present invention may be implemented by using hardware, software, or a combination of hardware and software, as desired. If implemented by software, a processor and a machine readable medium are required. The processor may be any type of processor capable of providing the speed and functionality required by the embodiments of the invention. Machine-readable memory includes any media capable of storing instructions adapted to be executed by a processor. Some examples of such memory include, but are not limited to, read-only memory (ROM), random-access memory (RAM), programmable ROM (PROM), erasable programmable ROM (EPROM), electronically erasable programmable ROM (EEPROM), dynamic RAM (DRAM), magnetic disk (e.g., floppy disk and hard drive), optical disk (e.g. CD-ROM), and any other device that can store digital information. The instructions may be stored on a medium in either a compressed and/or encrypted format. Accordingly, in the broad context of the present invention, and with attention to FIG. 6, a system and method for overlaying ultrasound imagery on a laparoscopic camera display in real time may contain a processor (610) and machine readable media (620) and user interface (630).

Although illustrative embodiments and methods have been shown and described, a wide range of modifications, changes, and substitutions is contemplated in the foregoing disclosure and in some instances some features of the embodiments or steps of the method may be employed without a corresponding use of other features or steps. Accordingly, it is appropriate that the claims be construed broadly and in a manner consistent with the scope of the embodiments disclosed herein.

What is claimed is:

1. A system comprising:
    a laparoscope configured to capture a laparoscopic image of a surgical field including texture elements $C_l$;
    a laparoscopic ultrasound probe configured to capture an ultrasonic image of a structure in the surgical field including texture elements $C_s$;
    a tracking system configured to detect a position and orientation of said laparoscope and a position and orientation of said laparoscopic ultrasound probe;
    data associated with said laparoscope wherein said data indicates a distortion in said laparoscopic image; and
    a computer configured to receive said laparoscopic image, said ultrasonic image and said distortion data associated with said laparoscope wherein said computer is configured to:
        position and orient said ultrasonic image relative to said laparoscopic image,
        adjust said ultrasonic image based upon said distortion data,
        combine texture elements of said adjusted ultrasonic image, $C_s$, with texture elements of said laparoscopic image, $C_l$, wherein said combined texture elements, $C_o$ are computed according to $C_o=tC_s+(1-t)C_l$, where t is a user specified translucency factor in the range of 0 to 1, and
        output said combined images.

2. The system of claim 1 wherein said distortion data comprises a measurement of a feature in said laparoscopic image that is attributed to a laparoscopic lens and not present in the surgical field.

3. The system of claim 2 wherein said distortion data comprises measurement of a degree of curvature.

4. The system of claim 1 wherein said computer is further configured to receive and process a user input.

5. The system of claim 4 wherein said computer is configured to receive said user input through a graphical user interface (GUI).

6. The system of claim 4 wherein said computer is further configured to adjust said position and said orientation of said ultrasonic image based upon said user input.

7. The system of claim 4 wherein said computer is further configured to annotate said ultrasonic image based on said user input.

8. The system of claim 1 wherein said computer is further configured to combine a plurality of adjusted ultrasonic images with said laparoscopic image.

9. A method for overlaying an ultrasonic image on a laparoscopic image, said method comprising:
    retrieving data associated with a laparoscope wherein said data indicates a distortion in said laparoscopic image;
    capturing said laparoscopic image of a surgical field including texture elements $C_l$ using said laparoscope;
    capturing said ultrasonic image of the surgical field including texture elements $C_s$ using a laparoscopic ultrasound probe;
    detecting a position and orientation of said laparoscope and a position and orientation of said ultrasound probe;
    positioning and orienting said ultrasonic image relative to said laparoscopic image;
    adjusting said ultrasonic image based upon said distortion data;
    combining texture elements of said adjusted ultrasonic image, $C_s$, with texture elements of said laparoscopic image, $C_l$, wherein said combined texture elements, $C_o$ are computed according to $C_o=tC_s+(1-t)C_l$, where t is a user specified translucency factor in the range of 0 to 1, and
    outputting said combined images.

10. The method of claim 9 wherein said distortion data comprises a measurement of a feature in said laparoscopic image that is attributed to a laparoscopic lens and not present in the surgical field.

11. The method of claim 10 wherein said distortion data comprises measurement of a degree of curvature.

12. The method of claim 9 further comprising displaying said combined images.

13. The method of claim 9 further comprising acquiring said data associated with said laparoscope.

14. The method of claim 9 further comprising combining a plurality of adjusted ultrasonic images with said laparoscopic image based on a user input.

15. The method of claim 9 further comprising adjusting said position and said orientation of said ultrasonic image based on a user input.

16. An article comprising a storage medium having stored thereon instructions that when executed by a machine result in the following operations for overlaying an ultrasonic image on a laparoscopic image:

retrieving data associated with a laparoscope wherein said data indicates a distortion in said laparoscopic image;

receiving said laparoscopic image of a surgical field including texture elements $C_l$ captured using said laparoscope;

receiving said ultrasonic image of the surgical field including texture elements $C_s$ captured using a laparoscopic ultrasound probe;

receiving a position and orientation of said laparoscope and a position and orientation of said ultrasound probe;

positioning and orienting said ultrasonic image relative to said laparoscopic image;

adjusting said ultrasonic image based upon said distortion data;

combining texture elements of said adjusted ultrasonic image, $C_s$, with texture elements of said laparoscopic image, $C_l$, wherein said combined texture elements, $C_o$ are computed according to $C_o=tC_s+(1-t)C_l$, where t is a user specified translucency factor in the range of 0 to 1, and outputting said combined images.

17. The article of claim 16 wherein said distortion data comprises a measurement of a feature in said laparoscopic image that is attributed to a laparoscopic lens and not present in the surgical field.

18. The article of claim 16 wherein said distortion data comprises measurement of a degree of curvature.

19. The article of claim 16 wherein said instructions when executed further comprise receiving and processing a user input; and combining a plurality of adjusted ultrasonic images with said laparoscopic image based on said user input.

* * * * *